US011191431B2

(12) United States Patent
Shimizu et al.

(10) Patent No.: US 11,191,431 B2
(45) Date of Patent: Dec. 7, 2021

(54) OPHTHALMIC APPARATUS

(71) Applicant: NIDEK CO., LTD., Gamagori (JP)

(72) Inventors: Kazunari Shimizu, Toyokawa (JP); Kenji Nakamura, Toyohashi (JP); Toru Arikawa, Nukata-gun (JP)

(73) Assignee: NIDEK CO., LTD., Gamagori (JP)

( * ) Notice: Subject to any disclaimer, the term of this patent is extended or adjusted under 35 U.S.C. 154(b) by 52 days.

(21) Appl. No.: 16/176,808

(22) Filed: Oct. 31, 2018

(65) Prior Publication Data

US 2019/0150735 A1 May 23, 2019

(30) Foreign Application Priority Data

Nov. 1, 2017 (JP) .............................. JP2017-212294

(51) Int. Cl.
*A61B 3/15* (2006.01)
*A61B 3/16* (2006.01)
(Continued)

(52) U.S. Cl.
CPC ............ *A61B 3/152* (2013.01); *A61B 3/0075* (2013.01); *A61B 3/103* (2013.01); *A61B 3/165* (2013.01); *A61B 3/102* (2013.01); *A61B 3/12* (2013.01)

(58) Field of Classification Search
CPC ... A61B 3/165; A61B 3/0075; A61B 13/1208; A61B 3/1216; A61B 3/1225;
(Continued)

(56) References Cited

U.S. PATENT DOCUMENTS

| 5,909,269 A | 6/1999 | Isogai et al. |
| 2004/0189936 A1* | 9/2004 | Mimura ................. A61B 3/165 351/205 |

(Continued)

FOREIGN PATENT DOCUMENTS

| EP | 3150111 A1 | 4/2017 |
| JP | H10-071122 A | 3/1998 |

(Continued)

OTHER PUBLICATIONS

Aug. 2, 2021 Office Action issued in Japanese Patent Application No. 2017-212294.

*Primary Examiner* — Marin Pichler
*Assistant Examiner* — Alberto J Betancourt
(74) *Attorney, Agent, or Firm* — Oliff PLC (57) ABSTRACT

An ophthalmic apparatus to examine an examinee's eye includes: a first optometry unit to perform a first examination of the examinee's eye; a second optometry unit to perform a second examination of the examinee's eye; a drive unit to cause relative movement of the first and second optometry units in three-dimensional manner relative to the examinee's eye; a controller to control the drive unit; a selection receiving unit to receive a selection signal representing at least one selected from the first second examinations; and a face photographing unit to photograph a face image including at least one of examinee's right and left eyes. The controller switches, according to the selection signal, between a first path for alignment of the first optometry unit with the eye detected from the face image and a second path for alignment of the second optometry unit with the eye detected from the face image.

7 Claims, 7 Drawing Sheets

(51) Int. Cl.
*A61B 3/103* (2006.01)
*A61B 3/00* (2006.01)
*A61B 3/10* (2006.01)
*A61B 3/12* (2006.01)

(58) Field of Classification Search
CPC ............... A61B 3/1233; A61B 3/1241; A61B 3/145–158; A61B 3/1005; A61B 3/1025; A61B 3/12–3/135; A61B 3/1035; A61B 3/185
USPC ........ 351/200, 205–208, 211–215, 220–221, 351/245–247; 396/18
See application file for complete search history.

(56) References Cited

U.S. PATENT DOCUMENTS

2009/0128778 A1* 5/2009 Honda ................... A61B 3/103 351/245
2016/0310003 A1* 10/2016 Inuzuka ................... A61B 3/10
2018/0055358 A1* 3/2018 Nakajima ............... A61B 3/152
2018/0353063 A1* 12/2018 Uji ........................... A61B 3/12

FOREIGN PATENT DOCUMENTS

| JP | H10-216089 A | 8/1998 |
| JP | 2007-282671 A | 11/2007 |
| JP | 2013-066760 A | 4/2013 |
| JP | 2017-064058 A | 4/2017 |

\* cited by examiner

FIG. 7B

OPHTHALMIC APPARATUS

CROSS-REFERENCE TO RELATED APPLICATIONS

This application is based upon and claims the benefit of priority from the prior Japanese Patent Application No. 2017-212294 filed on Nov. 1, 2017, the entire contents of which are incorporated herein by reference.

BACKGROUND

The present disclosure relates to an ophthalmic apparatus for examining an examinee's eye.

As a conventional ophthalmic apparatus, for example, there are known an eye refractive power measuring apparatus, a corneal curvature measuring apparatus, an intraocular pressure measuring apparatus, a fundus camera, a corneal endothelial cell photographing apparatus, an OCT, an SLO, and others. Those alignment are generally configured to move an optometry unit in up/down, right/left, and front/back directions relative to an examinee's eye by operation of an operation member, such as a joystick, to align the optometry unit at a predetermined position with respect to the examinee's eye (see Japanese unexamined patent application publication No. 2013-066760).

For the conventional ophthalmic apparatus, furthermore, there is proposed an apparatus configured to make rough alignment (rough position adjustment) of an optometry unit relative to an eye of an examinee based on a photographed image of the face of the examinee (see Japanese unexamined patent application publication No. 10-216089(1998)).

SUMMARY

However, a combined apparatus adapted to switch over an examination optical axis according to a measurement mode could not appropriately make rough alignment.

The present disclosure has been made to address the above problems and has a purpose to provide an ophthalmic apparatus capable of appropriately making alignment according to a measurement mode.

To achieve the above purpose, the present disclosure provides an ophthalmic apparatus configured to examine an eye of an examinee, the apparatus comprising: a first optometry unit configured to perform a first examination of the examinee's eye; a second optometry unit configured to perform a second examination of the examinee's eye; a drive unit configured to cause relative movement of the first optometry unit and the second optometry unit in three-dimensional manner with respect to the examinee's eye; a controller configured to control the drive unit; a selection receiving unit configured to receive a selection signal representing at least one selected from the first examination and the second examination; and a face photographing unit configured to photograph a face image including at least one of right and left eyes of the examinee, wherein the controller is configured to switch, according to the selection signal, between a first path for alignment of the first optometry unit with the examinee's eye detected from the face image and a second path for alignment of the second optometry unit with the examinee's eye detected from the face image.

DETAILED DESCRIPTION OF THE EXEMPLARY EMBODIMENTS

Embodiments

An embodiment of this disclosure will be explained below referring to accompanying drawings. An ophthalmic apparatus 1 (see FIG. 1) in the present embodiment is configured to examine an examinee's eye. This ophthalmic apparatus includes for example a first optometry unit (a first optometry unit 4a), a second optometry unit (a second optometry unit 4b), a drive unit (e.g. a drive unit 2), and a controller (e.g. a controller 20), a selection receiving unit (e.g. the controller 20), and a face photographing unit (e.g. a face photographing unit 190). The first optometry unit is for example configured to perform a first examination of an examinee's eye. The second optometry unit is for example configured to perform a second examination of the examinee's eye. These first optometry unit and second optometry unit may be selected from for example an eye refractive power measuring unit, a corneal shape measuring unit, an intraocular pressure measuring unit, a fundus photographing unit, a corneal endothelial cell photographing unit, an OCT, an SLO, and others.

The drive unit is for example configured to cause relative movement of the first optometry unit and the second optometry unit in a three-dimensional manner relative to the examinee's eye. The drive unit may also be configured to independently move each of the first optometry unit and the second optometry unit. The controller is configured to control the drive unit. The selection receiving unit is configured to receive a selection signal representing at least selected one of the first examination and the second examination. For instance, the selection receiving unit receives a selection signal indicating a selected examination to be performed on an examinee's eye. The selection receiving unit may also be configured to receive a selection signal indicating a selected examination to be performed first on an examinee's eye. The face photographing unit is configured to photograph an image of the face including at least one of right and left examinee's eyes, which will be referred to as a face image.

The controller is configured to switch, according to a selection signal, between a first path for alignment of the first optometry unit with the examinee's eye detected from the face image and a second path for alignment of the second optometry unit with the examinee's eye detected from the face image. Thus, the ophthalmic apparatus 1 can appropriately perform alignment at a position suitable for the selected examination.

The controller may also be configured to switch between a first direction (e.g. a direction V1) and a second direction (a direction V2) according to the selected examination. This enables good alignment to be performed even when the height of the optometry unit is changed over according to the selected examination.

The controller may also be configured to determine the first path based on the direction of the examinee's eye relative to the face photographing unit and the relative position between the face photographing unit and the first optometry unit. Further, the controller may also be configured to determine the second path based on the direction of the examinee's eye relative to the face photographing unit and the relative position between the face photographing unit and the second optometry unit. For instance, the controller may also determine the first path based on the direction of the examinee's eye obtained from the face image and a distance between the optical axis of the face photographing unit and the optical axis of the first optometry unit. Similarly, the controller may also determine the second path based on the direction of the examinee's eye obtained from the face image and a distance between the optical axis of the face photographing unit and the optical axis of the second optometry unit.

The controller may also be configured to set a moving speed to move the first optometry unit and the second optometry unit such that the moving speed is different between the first path and the second path. Accordingly, even when a plurality of optometry units are arranged, the alignment can be appropriately performed according to a target one of the optometry units.

An example is given that the first optometry unit is an eye refractive power measuring unit for measuring eye refractive power of an examinee's eye and the second optometry unit is an intraocular pressure measuring unit for measuring intraocular pressure of an examinee's eye. In this case, the moving speed of the optometry unit in the second path for alignment of the intraocular pressure measuring unit is set slower than the moving speed of the optometry unit in the first path for alignment of the eye refractive power measuring unit. This can reduce a feeling of fear caused when a nozzle of the intraocular pressure measuring unit comes near an examinee without lengthening an alignment time of the eye refractive power measuring unit.

The face photographing unit may also be placed at a height between the first optical axis (an optical axis La) corresponding to the examination optical axis of the first optometry unit and the second optical axis (an optical axis Lb) corresponding to the examination optical axis of the second optometry unit. This enhances the possibility that the examinee's eye falls within a photographing range of the face photographing unit in both the case where the first optical axis is adjusted to the height of the examinee's eye and the case where the second optical axis is adjusted to the examinee's eye.

EXAMPLES

The ophthalmic apparatus of the present disclosure will be described below referring to the accompanying drawings. In the following description, the ophthalmic apparatus is embodied as a combined apparatus of an eye refractive power measuring apparatus and a non-contact tonometer. The ophthalmic apparatus however may also be a combined apparatus of at least two selected from a corneal curvature measuring apparatus, a corneal shape measuring apparatus, an intraocular pressure measuring apparatus, an axial length measuring apparatus, a fundus camera, an OCT (Optical Coherence Tomography), an SLO (Scanning Laser Ophthalmoscope) and others.

<Outer Appearance>

Figure 1:
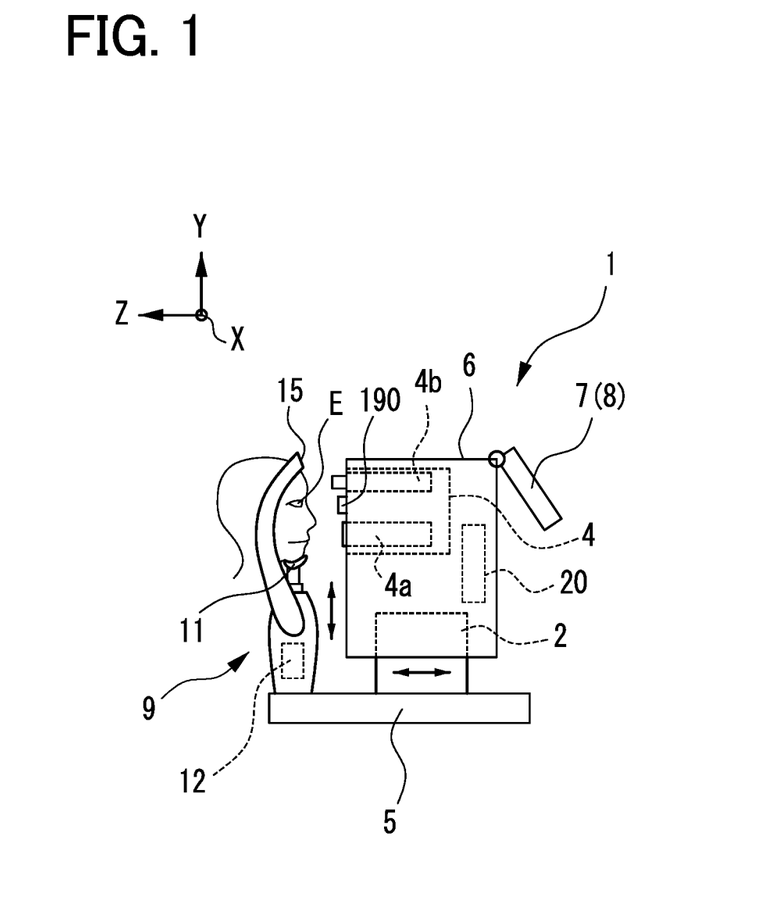
FIG. 1 is a schematic diagram showing outer appearance of an ophthalmic apparatus.

The outer appearance of the ophthalmic apparatus will be explained below referring to FIG. 1. As shown in FIG. 1, the ophthalmic apparatus 1 in the present example mainly includes an optometry unit 4, the face photographing unit 190, the drive unit 2, and the controller 20. The optometry unit 4 in this example is configured to measure eye refractive power and intraocular pressure of an examinee's eye E. The optometry unit 4 includes for example the first optometry unit 4a and the second optometry unit 4b. The first optometry unit 4a is configured to measure the eye refractive power of the examinee's eye E and the second optometry unit 4b is configured to measure the intraocular pressure of the examinee's eye E in non-contact relation.

The face photographing unit 190 is for example configured to photograph the face of an examinee. Specifically, the face photographing unit 190 photographs the face including at least one of right and left eyes E of the examinee. The drive unit 2 is for example configured to move the optometry unit 4 and the face photographing unit 190 relative to a base table 5 in up/down, right/left, and front/back directions (in a three-dimensional direction). The controller 20 is configured to control each part of the ophthalmic apparatus 1.

The ophthalmic apparatus 1 may include a housing 6, a display unit 7, an operation unit 8, a face support unit 9, and others. For example, the housing 6 houses the optometry unit 4, the face photographing unit 190, the drive unit 2, the controller 20, and others. The display unit 7 is for example configured to display an observation image and a measured result of the examinee's eye E, and others. The display unit 7 may be provided integrally with the ophthalmic apparatus 1 or separately from the ophthalmic apparatus 1. The operation unit 8 is used to enter various settings in the ophthalmic apparatus 1, operate the ophthalmic apparatus 1 at the start of measurement, and others. The operation unit 8 allows an examiner to input various operational instructions. The operation unit 8 in the present example is a touch panel. As an alternative, it may be selected from various types of human interface, such as a joystick, a mouse, a keyboard, a track ball, a button. Furthermore, a tablet computer may be used as the display unit 7 and the operation unit 8. The face support unit 9 may include for example a forehead rest 15 and a chin rest 11. The chin rest 11 may be configured to move up and down by driving of a chin-rest drive unit 12.

<Optometry Unit>

Figure 2:
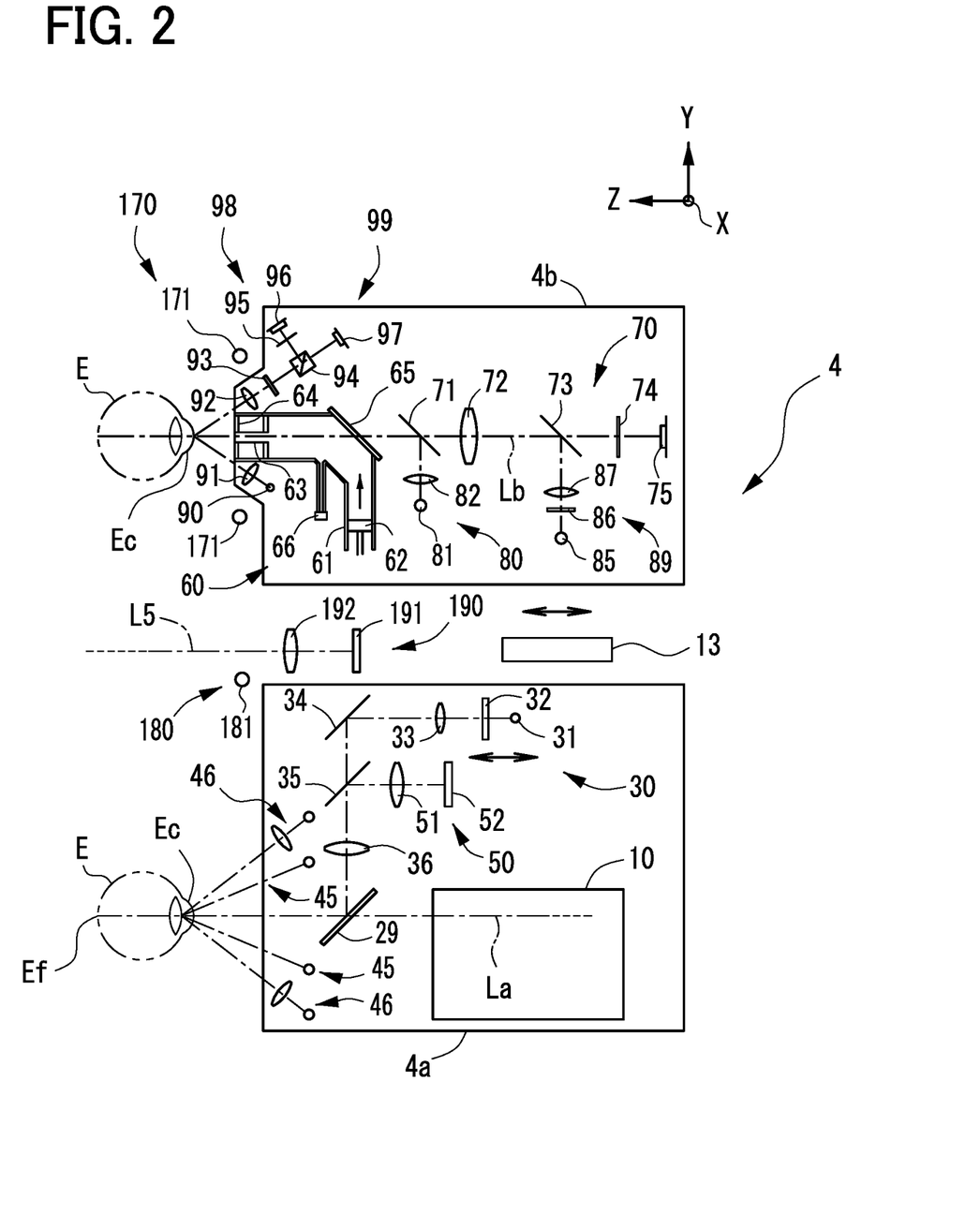
FIG. 2 is a schematic diagram showing optical systems of the ophthalmic apparatus.

The optometry unit 4 is for example configured to examine or photograph the examinee's eye E. As shown in FIG. 2, this optometry unit 4 in the present example includes the first optometry unit 4a configured to measure eye refractive power of the examinee's eye E and the second optometry unit 4b configured to measure intraocular pressure in non-contact relation. For example, the second optometry unit 4b is stacked on or above the first optometry unit 4a. Specifically, the measurement optical axis La of the first optometry unit 4a and the measurement optical axis Lb of the second optometry unit 4b are located at different heights relative to the examinee's eye E. The ophthalmic apparatus 1 is operated to align each of the measurement optical axis La and the measurement optical axis Lb with the examinee's eye E. The second optometry unit 4b may be placed to be movable in the Z direction relative to the first optometry unit 4a by driving of a Z-drive unit 13. For instance, during use of the second optometry unit 4b (during measurement of intraocular pressure), the second optometry unit 4b is used such that a nozzle 63 provided in the second optometry unit 4b protrudes toward the examinee's eye E more than the foremost surface of the first optometry unit 4a.

Firstly, the first optometry unit 4a is described below. This first optometry unit 4a mainly includes for example an eye refractive power measuring optical system 10, a first fixation target optical system 30, first target optical systems 45, second target optical systems 46, and a first observation optical system 50.

The eye refractive power measuring optical system 10 is configured to measure the eye refractive power of the examinee's eye E. This measuring optical system 10 consists of a projecting optical system for projecting a spot-shaped measurement target onto a fundus Ef of the eye E through a center portion of a pupil of the eye E and a light receiving optical system for taking a fundus reflection light in a ring shape reflected from the fundus Ef through a peripheral portion of the pupil and then capturing a ring-shaped fundus reflection image on a two-dimensional imaging element. The output from this two-dimensional imaging element is inputted to the controller 20.

A dichroic mirror 29, which allows measurement light to be used in the measurement optical system 10 to pass through, serves to direct fixation target light from the first fixation target optical system 30 toward the eye E and direct reflection light from an anterior segment of the examinee's eye E toward the first observation optical system 50.

The first fixation target optical system 30 includes a visible light source 31 for presenting a fixation target, a fixation target plate 32 having the fixation target, a light projecting lens 33, a total reflecting mirror 34, a dichroic mirror 35, and an objective lens 36 for observation. Light from this optical system 30 is made coaxial with the optical axis La by the dichroic mirror 29. The dichroic mirror 35 has the property of allowing visible light to pass through and reflecting infrared light. In this case, the fixation target light source 31 is positioned in an optically conjugate relationship with the fundus Ef. The light source 31 and the fixation target plate 32 are moved in an optical axis direction to fog the examinee's eye E.

The first target optical systems 45 are placed in front of the anterior segment of the eye E and configured to emit near infrared light to project a ring target onto a cornea Ec of the eye E. Further, the second target optical systems 46 are placed symmetric with respect to the optical axis La and configured to emit near infrared light to project infinite targets onto the cornea Ec of the eye E to detect an alignment state in a working distance direction with respect to the examinee's eye E. The first target optical systems 45 are not only used as a projecting optical system for projecting a ring-shaped target for measurement of corneal shape of an examinee's eye but also used to project an alignment detecting target and illuminate an anterior segment of the eye E.

The first observation optical system 50 shares the objective lens 36 and the dichroic mirror 35 of the first fixation target optical system 30 and includes an imaging lens 51 and a two-dimensional imaging element 52 each placed on the optical axis of light in a reflection direction of the dichroic mirror 35. Output from the imaging element 52 is inputted to the controller 20. Thus, an anterior segment image of the examinee's eye E is captured by the two-dimensional imaging element 52 and displayed on the display unit 7. The first observation optical system 50 also serves as an imaging optical system for capturing a ring target image formed on the cornea Ec of the examinee's eye E and alignment target images formed by the second target optical systems 46. Thus, the positions of the ring target image and the alignment target images are detected by the controller 20.

Secondly, the second optometry unit 4b is described below. This second optometry unit 4b includes for example a fluid spraying unit 60, an illumination optical system 170, a second observation optical system 70, a third target optical system 80, a second fixation target optical system 89, a deformation detecting optical system 98, a Z-alignment detecting system 99.

The fluid spraying unit 60 is configured to spray a fluid, such as air, onto the cornea of an examinee's eye. This fluid spraying unit 60 includes for example a cylinder 61, a piston 62, the nozzle 63, a glass plate 64, a glass plate 65, a pressure sensor 66, and others. The cylinder 61 is configured to compress air. The piston 62 is movable within the cylinder 61 by driving force of an unillustrated solenoid. The air compressed in the cylinder 61 by movement of the piston 62 is ejected toward the cornea Ec of the examinee's eye E through the nozzle 63. The glass plate 64 is made of transparent glass and configured to hold the nozzle 63. The glass plate 65 is made of transparent glass and placed behind the nozzle 63. Behind the glass plate 65, there are arranged optical systems for observation and alignment which will be mentioned later. The pressure sensor 66 is configured to detect the internal pressure of the cylinder 61. A detection signal from the pressure sensor 66 is transmitted to the controller 20 and utilized for calculation of an intraocular pressure value.

The illumination optical system 170 is configured to illuminate the anterior segment. This illumination optical system 170 includes for example infrared light sources 171 consisting of four light sources arranged around the optical axis Lb corresponding to the center axis of the nozzle 63.

The second observation optical system 70 is configured to photograph an anterior segment image of the examinee's eye E. This second observation optical system 70 includes a half mirror 71, an objective lens 72, a dichroic mirror 73, a filter 74, a two-dimensional imaging element 75, and others. An anterior segment image of the examinee's eye E formed by the light sources 171 passes through the glass plate 65, the half mirror 71, the objective lens 72, the dichroic mirror 73, and the filter 74, each placed on the optical axis Lb, and then is captured by the two-dimensional imaging element 75. The dichroic mirror 73 has the property of allowing infrared light to pass through and reflecting visible light. Further, the filter 74 has the property of allowing light from the light sources 171 and a light source 81 mentioned later to pass through and not allowing light from a light source 90 mentioned later to pass through. The anterior segment image captured by the two-dimensional imaging element 75 is inputted to the controller 20 and then displayed on the display unit 7.

The third target optical system 80 includes the infrared light source 81, a projection lens 82, and others. The infrared light source 81 is a light source for alignment in an X direction and a Y direction. Light from this light source 81 is projected onto the cornea Ec from front through the projection lens 82, the half mirror 71, and the glass plate 65. A corneal reflection image by the light source 81 is captured by the imaging element 75 through components from the glass plate 65 to the filter 74. An imaging signal from the imaging element 75 is inputted to the controller 20 and utilized for alignment in the X direction and the Y direction. The corneal reflection image by the light sources 171 can also be utilized for alignment in the X direction and the Y direction (for the details, refer to Japanese unexamined patent application publication No. 10-71122(1998) filed by the applicant).

The second fixation target optical system 89 includes a visible light source 85 for projecting a fixation target. Light of a fixation target 86 illuminated by the light source 85 travels to the examinee's eye E via a projection lens 87, a dichroic mirror 73, the objective lens 72, the half mirror 71, and the glass plate 65.

The deformation detecting optical system 98 is configured to detect a deformed state of a cornea. This deformation detecting optical system 98 includes for example the infrared light source 90, a collimator lens 91, a light receiving lens 92, a filter 93, a half mirror 94, a pinhole plate 95, a photodetector 96, and others. Light from the light source 90 is collimated into substantial parallel light beams by the collimator lens 91 and then projected on the cornea Ec. A corneal reflection image by the light source 90 is received by the photodetector 96 via the light receiving lens 92, the filter 93, the half mirror 94, and the pinhole plate 95. The filter 93 has the property of allowing light from the light source 90 to pass through and not allowing light from the light sources 85 and 81 to pass through. The deformation detecting optical system 98 is placed such that the amount of light received by the photodetector 96 is maximum when the cornea Ec is in a predetermined deformed state (an applanated state). A detection signal from the photodetector 96 is inputted to the controller 20 and used for calculation of an intraocular pressure value.

The Z-alignment detecting system 99 is configured to detect a working distance of the second optometry unit 4b with respect to the examinee's eye E. This Z-alignment detecting system 99 includes a one-dimensional position detecting element 97, and the light source 90 and the collimator lens 91 both of which are used in common by the deformation detecting optical system 98. The position detecting element 97 is for example a PSD, a linear sensor, or the like. A corneal reflection image by the light source 90 enters the position detecting element 97 through components from the light receiving lens 92 to the half mirror 94. A detection signal from the position detecting element 97 is inputted to the controller 20 and utilized for detection of alignment in the Z direction. Specifically, when the examinee's eye E (the cornea Ec) moves in the Z direction, the position of incidence of the corneal reflection image by the light source 90 also moves on the position detecting element 97. Thus, the alignment state in the Z direction with respect to the examinee's eye E can be detected based on a detection signal from the position detecting element 97.

In FIG. 2, for convenience of explanation, the optical systems for detecting corneal deformation and detecting a working distance are illustrated as if they are placed vertically. However, in fact, those optical systems are placed side by side in a horizontal direction with respect to an examinee's eye.

<Face Photographing Unit>

The face photographing unit 190 is for example an optical system configured to photograph the face of an examinee including at least one of right and left eyes of the examinee. For example, as shown in FIG. 2, the face photographing unit 190 in the present example mainly includes an imaging element 191 and an imaging lens 192.

Figure 3:
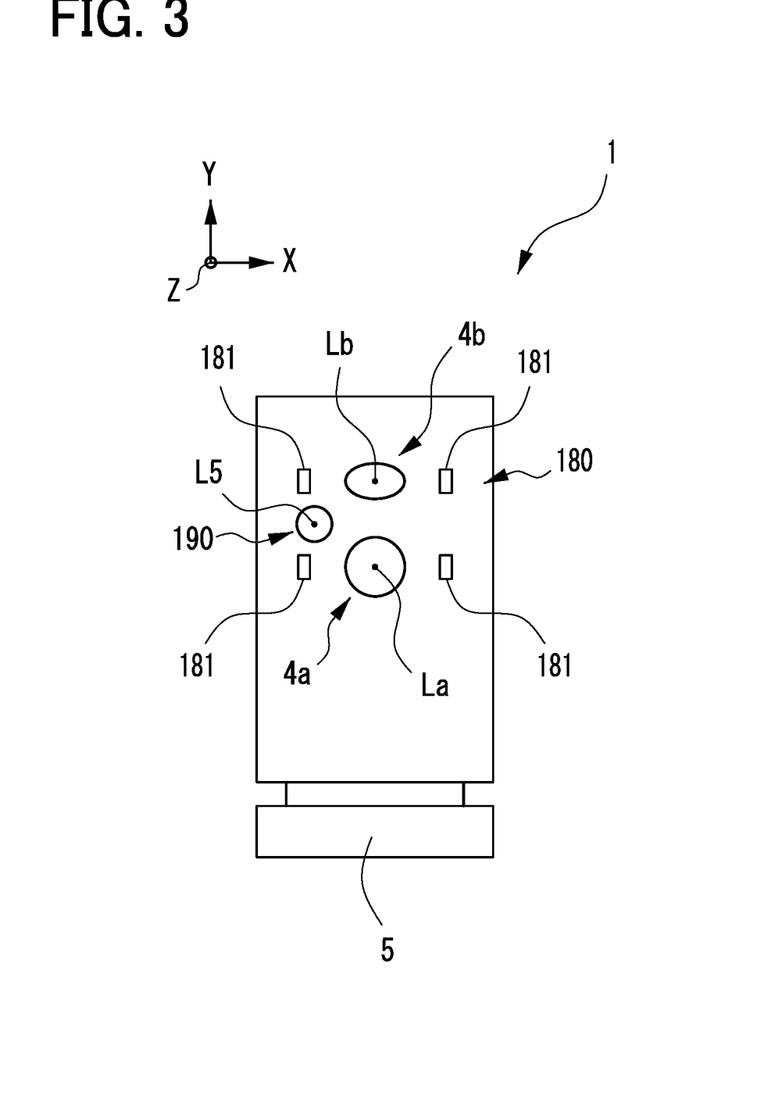
FIG. 3 is a schematic diagram showing an optometry unit as seen from an examinee side.

The face photographing unit 190 is placed in a position where it can photograph both eyes of an examinee for example when the optometry unit 4 is located at an initial position. In the present example, the initial position of the optometry unit 4 is set at a position displaced to the right with respect to the optical axis La (or the optical axis Lb) of the optometry unit 4 to facilitate an examination of the right eye (see FIG. 3). Accordingly, the face photographing unit 190 is placed in the position to photograph both eyes of an examinee while the optometry unit 4 is located at the initial position displaced to the right. For instance, the face photographing unit 190 is placed at a mechanical center when the optometry unit 4 is at the initial position. When this initial position is set for example based on half of the interpupillary distance, that is, based on the interpupillary distance of one eye, the face photographing unit 190 may be placed in a position displaced to the right/left by the one-eye interpupillary distance from the mechanical center of the apparatus body. An average value of the one-eye interpupillary distance is about 32 mm.

Moreover, the face photographing unit 190 is placed at the height between the first optometry unit 4a and the second optometry unit 4b. This means that the height of the optical axis L5 of the face photographing unit 190 is higher than the optical axis La and lower than the optical axis Lb. Since the face photographing unit 190 is placed at the height between the first optometry unit 4a and the second optometry unit 4b, the face photographing unit 190 can appropriately photograph the examinee's face in both cases where the optical axis La is adjusted to the height of the examinee's eye and where the optical axis Lb is adjusted to the examinee's eye.

The face photographing unit 190 in the present example is moved together with the optometry unit 4 by the drive unit 2. As an alternative, the face photographing unit 190 may also be held against movement and fixed on the base table 5.

The imaging lens 192 may be a wide-angle lens, for example. This wide-angle lens includes for example a fisheye lens, a conical lens, and others. With the wide-angle lens, the face photographing unit 190 can photograph the examinee's face at a wide angle of view.

<Face Illumination Optical System>

The face illumination optical system 180 is configured to illuminate the face of an examinee. This face illumination optical system 180 includes for example illumination light sources 181. The illumination light sources 181 emit infrared light. In the present example, the illumination light sources 181 are arranged at right and left positions of an inspection window. The light sources used in the face illumination optical system 180 have lower directivity than a light source for alignment target.

<Control System>

Figure 4:
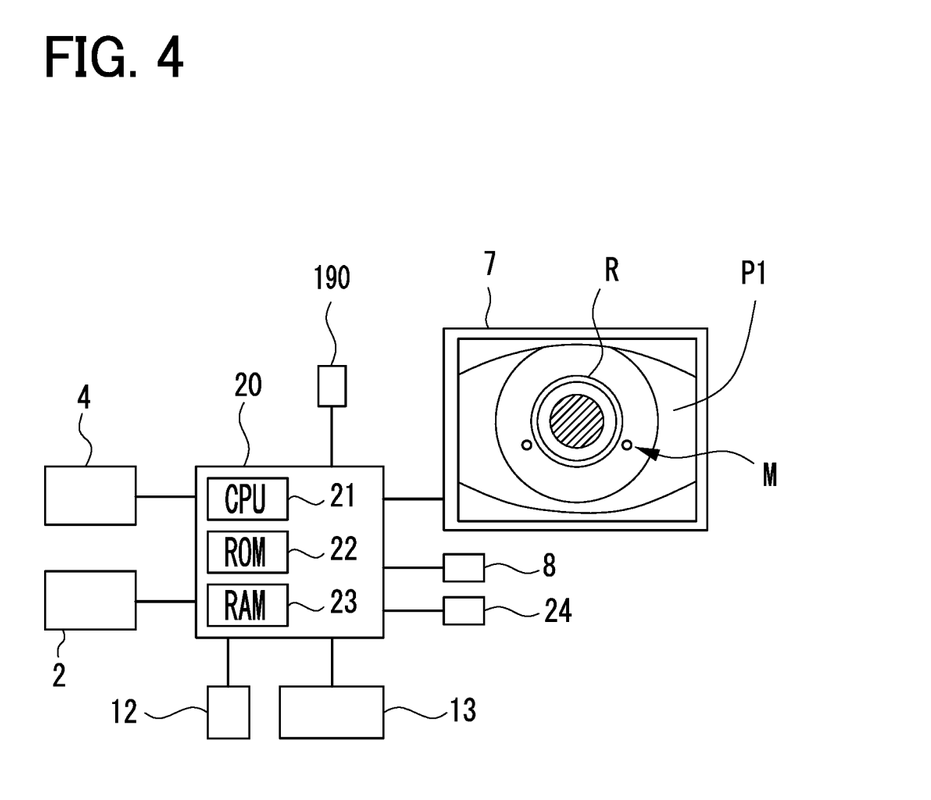
FIG. 4 is a block diagram showing a control system of the ophthalmic apparatus.

As shown in FIG. 4, the present apparatus 1 includes the controller 20. This controller 20 performs various controls of the present apparatus 1. The controller 20 includes for example a general CPU (Central Processing Unit) 21, a ROM 22, a RAM 23, and others. For instance, the ROM 22 stores an ophthalmic apparatus control program, initial value(s), and others to control the ophthalmic apparatus 1. For instance, the RAM 23 temporarily stores various types of information. The controller 20 is connected to the optometry unit 4, the face photographing unit 190, the drive unit 2, the Z-drive unit 13, the display unit 7, the operation unit 8, the chin-rest drive unit 12, a storage part (e.g. a non-volatile memory) 24, and others. The storage part 24 is for example a non-transitory storage medium that can retain stored content(s) even when power supply is shut down. As this storage part 24, a hard disc drive, a detachable USB flash memory, and others can be used.

<Control Operation>

Control operations in the ophthalmic apparatus configured as above will be described below. The ophthalmic apparatus 1 includes for example a plurality of measurement modes and operates according to each of the measurement modes. For instance, the modes include a first mode of measuring refractive power of each examinee by use of the first optometry unit 4a, a second mode of measuring intraocular pressure of each examinee by use of the second optometry unit 4b, and a third mode of measuring refractive power and intraocular pressure of each examinee by use of the first optometry unit 4a and the second optometry unit 4b. The controller 20 is for example configured to automatically perform position adjustment (alignment) of the first optometry unit 4a or the second optometry unit 4b with respect to an examinee's eye according to each measurement mode and conduct corresponding measurements. The following explanation is made on the outline of the control operations of the ophthalmic apparatus 1 with referring to FIG. 5.

(Step S1: Receipt of Selection Signal)

Figure 5:
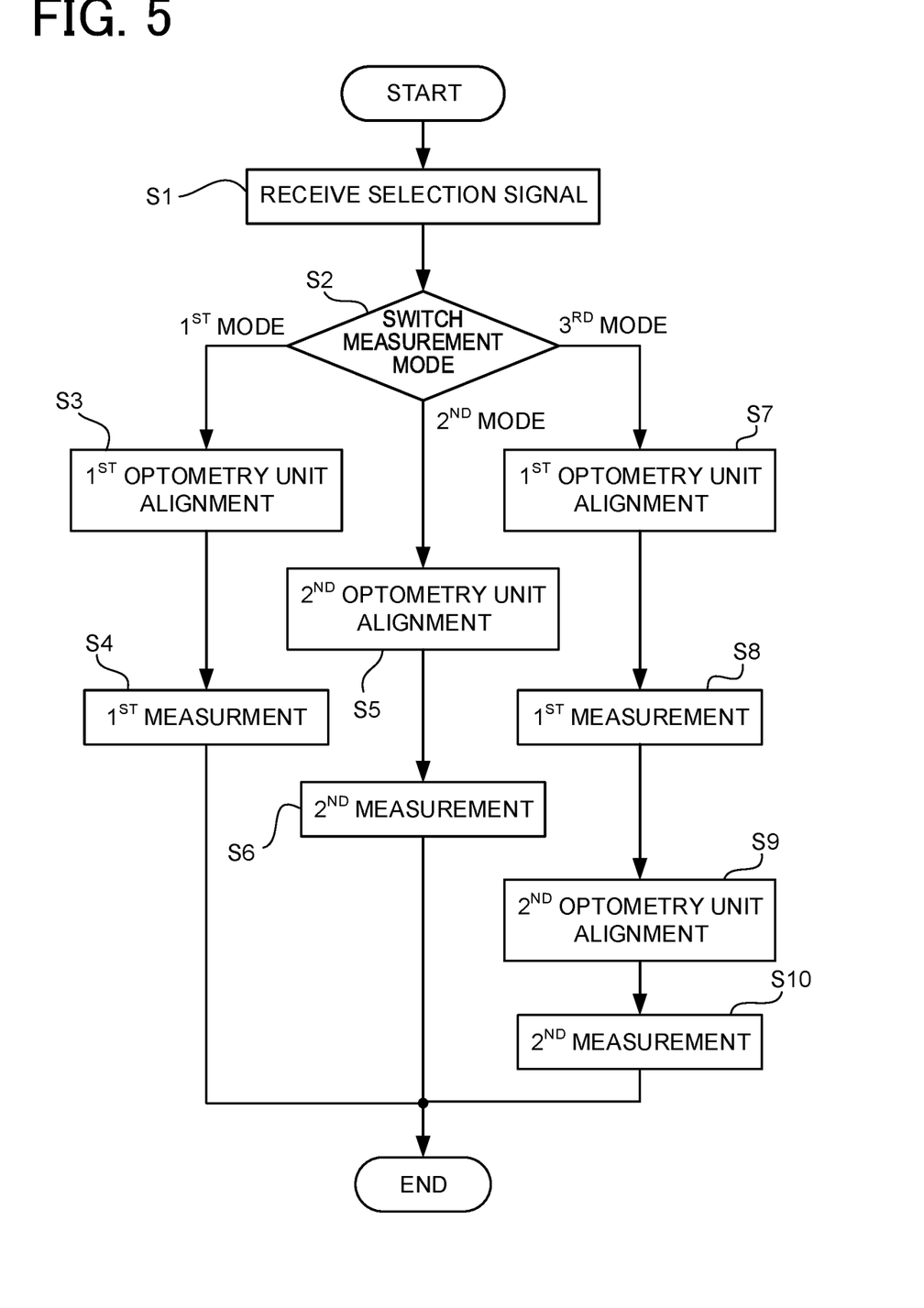
FIG. 5 is a flowchart schematically showing measuring operations of the ophthalmic apparatus.

The controller 20 firstly receives a selection signal representing a selected measurement mode from the operation unit 8 according to an operation of an examiner.

(Step S2: Switching of Measurement Mode)

Upon receipt of the selection signal, the controller 20 switches the measurement mode based on the received selection signal. For example, when the first mode is selected by the examiner, the controller 20 switches the measurement mode to the first mode. In the first mode, the controller 20 drives the drive unit 2 to adjust the measurement optical axis La of the first optometry unit 4a at almost the same height or level as the examinee's eye E (Rough adjustment suffices). In this case, the controller 20 adjusts the height position of the optometry unit 4 such that the measurement optical axis La becomes almost the same height as an eye level check line, not illustrated in the figure, formed in the face support unit 9. Further, the controller 20 drives the Z-drive unit 13 to retract the second optometry unit 4b inward the apparatus body relative to the first optometry unit 4a, that is, to move the second optometry unit 4b in a direction back away from the examinee's eye E, in order to prevent the tip of the nozzle 63 from touching an examinee's forehead and others during refractive power measurement. Accordingly, the optometry unit 4 is transformed to the apparatus configuration capable of measuring refractive power. Further, the controller 20 is preferably configured to drive the drive unit 2 to move the optometry unit 4 in advance to an original position relative to the base table 5.

When the second mode is selected by the examiner, the controller 20 switches the measurement mode to the second mode and drives the drive unit 2 to adjust the optical axis Lb at almost the same height as the examinee's eye E. Further, the controller 20 drives the Z-drive unit 13 to move forward the second optometry unit 4b relative to the first optometry unit 4a, that is, to move the second optometry unit 4b in a direction toward the examinee's eye E, such that the tip of the nozzle 63 protrudes toward the examinee relative to the front surface of the first optometry unit 4a. Thus, the optometry unit 4 is transformed to the apparatus configuration capable of measuring intraocular pressure.

When the third mode is selected, the controller 20 drives the drive unit 2, as in the first mode, to move the optometry unit 4 in the up/down, or vertical, direction to adjust the measurement optical axis La of the first optometry unit 4a at almost the same height as the examinee's eye E. Changing the height of the optometry unit 4 for each mode as above enables to reduce the moving amount of the optometry unit 4 in the vertical direction during alignment.

(Step S3: Alignment of First Optometry Unit)

Figure 6:
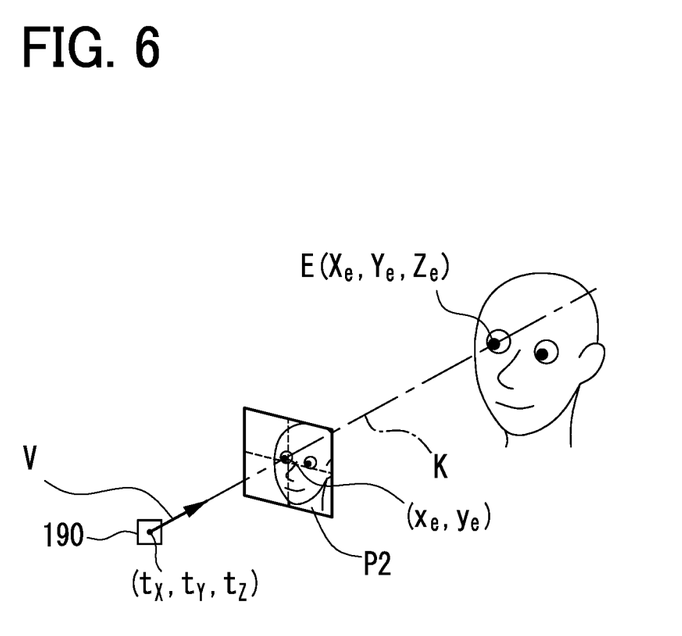
FIG. 6 is a diagram showing a direction of an examinee's eye as seen from a face photographing unit.

In step S2, when the measurement mode is switched to the first mode, the controller 20 makes alignment of the first optometry unit 4a with respect to the examinee's eye E. In this case, firstly, the controller 20 causes the face photographing unit 190 to photograph a face image P2 of the examinee (see FIG. 6). Then, the controller 20 calculates the direction V1 of the examinee's eye E as seen from the face photographing unit 190 (see FIG. 7A). The controller 20 moves the optometry unit 4 based on the calculated direction V1. A method of calculating the examinee's eye direction will be described later.

Figure 7A:
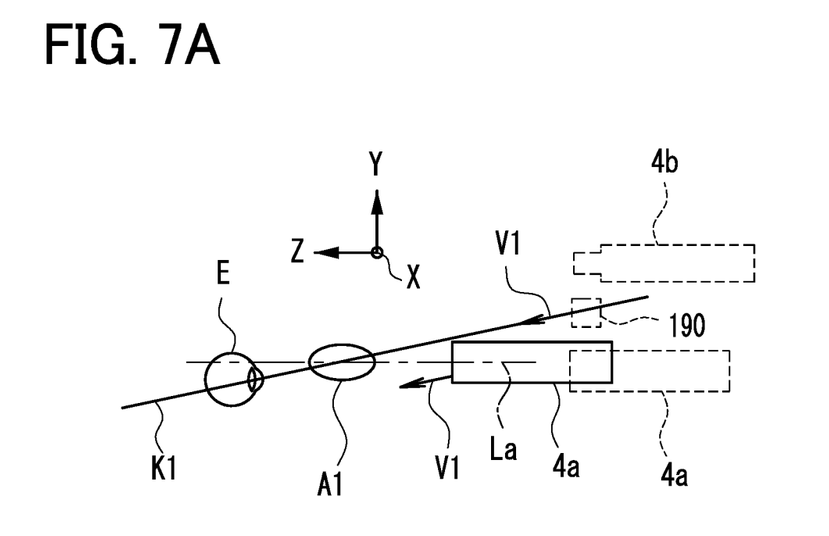
FIGS. 7A and 7B are diagrams to explain alignment operation of the optometry unit.

For instance, the controller 20 moves an alignment allowable region A1 of the first optometry unit 4a along a straight line K1 passing through the position of the face photographing unit 190 and extending in the direction V1. Herein, the alignment allowable region A1 is for example a region where the first optometry unit 4a can detect the three-dimensional position of an examinee's eye. The positional relationship between the position of the face photographing unit 190 and the alignment allowable region A1 is known in terms of apparatus design. Accordingly, the controller 20 can move the alignment allowable region A1 along the straight line K1 as shown in FIG. 7A. As above, since the controller 20 can move the optometry unit 4 through a path along the straight line K1 such that for example the alignment allowable region A1 includes at least a part of the straight line K1, it is possible to position the examinee's eye E into the alignment allowable region A1.

When the optometry unit 4 is moved as above until the examinee's eye E1 falls in the alignment allowable region A1, a ring target R formed by the first target optical systems 45 and infinite target images M formed by the second target optical systems 46 come into a state imagable by the imaging element 52 (see FIG. 4). At that time, the controller 20 can detect an alignment state of the first optometry unit 4a in the up/down and right/left directions and front/back direction relative to the examinee's eye. The controller 20 therefore controls driving of the drive unit 2 based on an alignment detection result to automatically move the optometry unit 4 in each of X, Y, and Z directions to perform the detailed position adjustment between the examinee's eye E and the first optometry unit 4A.

In this case, for instance, the controller 20 can obtain an amount of misalignment of the first optometry unit 4 in the up/down and right/left directions relative to the examinee's eye by calculating the coordinate of the center point of the ring target R detected from the anterior segment image P photographed by the imaging element 52. Furthermore, the controller 20 can obtain an alignment amount (a misalignment amount) of the first optometry unit 4a in a working distance direction relative to the examinee's eye E by utilizing the property that when the optometry unit 4 is displaced in the Z (working distance) direction relative to the examinee's eye E, an interval between the infinite targets M on a cornea formed by the second target optical system 46 hardly changes, whereas an image interval in a predetermined meridian direction varies.

(Step S4: First Measurement)

In step S3, when the alignment of the first optometry unit 4a with the examinee's eye E is completed, the controller 20 causes the first optometry unit 4a to measure the refractive power of the examinee's eye E. For instance, the controller 20 turns on a measurement light source of the measurement optical system 10 based on input of a measurement start signal. Measurement light emitted from the measurement light source is projected onto the fundus Ef of the examinee's eye through an unillustrated light projecting optical system of the measurement optical system 10 and the dichroic mirror 29, thereby forming a spot-shaped image of a point light source onto the fundus Ef.

The light of the point-light-source image formed on the fundus Ef is reflected and scattered, and then emerges from the examinee's eye E and passes through the dichroic mirror 29. Thereafter, this light is received as a ring image by an imaging element through an unillustrated light receiving optical system of the measurement optical system 10.

At that time, a preliminary measurement of eye refractive power is first conducted. Based on a result of this premeasurement, the light source 31 and the fixation target plate 32 are moved in the optical axis direction to fog the examinee's eye E. Then, the measurement of eye refractive power is performed on the fogged examinee's eye.

An output signal from an imaging element of the measurement optical system 10 is stored as image data in the storage unit 24. Successively, the controller 20 calculates each of eye refractive value, S (sphere power), C (cylinder power), and A (astigmatic axial angle) of the examinee's eye based on the ring image stored in the storage unit 24, and displays the measured result on the display unit 7. When a predetermined number (e.g. three) of measurement values excepting measurement errors are obtained, the eye refractive power measurement is terminated. Then, the controller 20 for example moves the optometry unit 4 to an initial position in the first mode and stops controlling.

(Step S5: Alignment of Second Optometry Unit)

In step S2, when the measurement mode is switched to the second mode, the controller 20 makes alignment of the second optometry unit 4b with respect to the examinee's eye E. For alignment of the second optometry unit 4b, the controller 20 also calculates the direction V2 of the examinee's eye E based on a face image P2 photographed by the face photographing unit 190 (see FIG. 7B). Herein, the initial position of the optometry unit 4 differs between the first mode and the second mode, resulting in a difference in the direction of the examinee's eye as seen from the face photographing unit 190. The controller 20 calculates the direction V2 of the examinee's eye E in the second mode and moves the optometry unit 4 based on this direction V2.

Figure 7B:
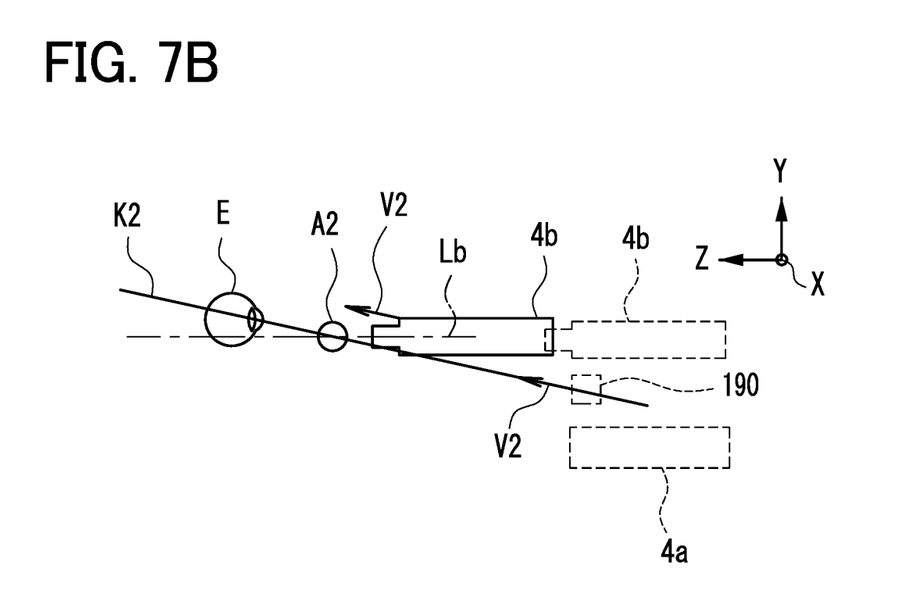

For instance, the controller 20 moves an alignment allowable region A2 of the second optometry unit 4b along a straight line K2 passing through the position of the face photographing unit 190 and extending in the direction V2. Herein, the alignment allowable region A2 is for example a region where the second optometry unit 4b can detect the three-dimensional position of an examinee's eye. The positional relationship between the position of the face photographing unit 190 and the alignment allowable region A2 is known in terms of apparatus design. Accordingly, the controller 20 can move the alignment allowable region A2 along the straight line K2 as shown in FIG. 7B. As above, since the controller 20 can move the optometry unit 4 through a path along the straight line K2 such that for example the alignment allowable region A2 includes at least a part of the straight line K2, it is possible to position the examinee's eye E into the alignment allowable region A2.

When the optometry unit 4 is moved as above until the examinee's eye E falls in the alignment allowable region A2, a corneal reflection image formed by the light source 90 comes to enter the position detecting element 97. The controller 20 thus controls driving of the drive unit 2 based on the detection result of the position detecting element 97 to perform detailed alignment in the Z direction. The controller 20 further controls driving of the drive unit 2 based on the detection result obtained by the imaging element 75 about the corneal reflection image formed by the light source 81 to perform detailed alignment in the X direction and the Y direction.

When the second optometry unit 4b is to be aligned with the examinee's eye, the moving speed to move the optometry unit 4 may be set slower than the moving speed set when the first optometry unit 4a is to be aligned with the examinee's eye. For instance, as shown in the present example, when the working distance of the second optometry unit 4b for measuring intraocular pressure is shorter than that of the first optometry unit 4a for measuring refractive power, the nozzle 63 of the fluid spraying unit 60 may touch the examinee. Therefore, as described above, the moving speed of the optometry unit 4 for alignment of the first optometry unit 4a is set different from the moving speed of the optometry unit 4 for alignment of the second optometry unit 4b, thereby enabling the alignment of the second optometry unit 4b to be safely performed without increasing the length of time required to perform alignment of the first optometry unit 4a.

(Step S6: Second Measurement)

In step S5, when the alignment of the second optometry unit 4b with the examinee's eye is completed, the controller 20 causes the second optometry unit 4b to measure the intraocular pressure of the examinee's eye. For instance, the controller 20 drives an unillustrated solenoid. When the piston 62 is moved by driving of the solenoid, the air in the cylinder 61 is compressed and thus the compressed air is sprayed toward the cornea Ec through the nozzle 63. The cornea Ec is gradually deformed by the sprayed compressed air and, when the cornea Ec comes to an applanated state, a maximum quantity of light enters the photodetector 96. The controller 20 then calculates an intraocular pressure value based on the output signal from the pressure sensor 66 and the output signal from the photodetector 96. This measured result is displayed on the display unit 7. Herein, when a predetermined condition for termination of measurement is satisfied, the intraocular pressure measurement of the examinee's eye is regarded as being completed. Then the controller 20 for example moves the optometry unit 4 to an initial position in the second mode and stops controlling.

(Step S7: Alignment of First Optometry Unit)

In step S2, when the measurement mode is switched to the third mode, the controller 20 makes alignment of the first optometry unit 4a with respect to the examinee's eye E in the same manner as in step S3.

(Step S8: First Measurement)

In step S7, when alignment of the first optometry unit 4a with the examinee's eye is completed, the controller 20 causes the first optometry unit 4a to measure the refractive power of the examinee's eye in the same manner as in Step S4.

(Step S9: Alignment of Second Optometry Unit)

Upon completion of the first measurement, the controller 20 performs alignment of the second optometry unit 4b with the examinee's eye. At that time, the controller 20 may move the optometry unit 4 in the vertical direction by an optical axis interval distance, which is a known value, in the vertical direction between the measurement optical axis La and the measurement optical axis Lb to make rough alignment. In this case, for example, the ophthalmic apparatus 1 may include a position detecting unit (e.g. an encoder) for detecting the position of the optometry unit 4. For instance, this position detecting unit may be configured to detect the positional information of the optometry unit 4 when the first measurement is performed. The controller 20 may be configured to perform position adjustment of the second optometry unit 4b based on the positional information of the optometry unit 4 in the first measurement, the relative positional information of the first optometry unit 4a and the second optometry unit 4b, and an appropriate working distance of the second optometry unit 4b.

(Step S10: Second Measurement)

Upon completion of alignment of the second optometry unit 4b with the examinee's eye, the controller 20 causes the second optometry unit 4b to measure the intraocular pressure of the examinee's eye in the same manner as in step S6.

The ophthalmic apparatus 1 in the present example obtains the direction of the examinee's eye through the face photographing unit 190 and switches a movement path of the optometry unit 4 according to each measurement mode. Accordingly, even a combined apparatus including a plurality of examination optical axes can perform fully automatic alignment. Furthermore, since the ophthalmic apparatus 1 can perform automatic alignment of a plurality of optometry units even by using a single face photographing unit 190, the apparatus can be designed with a simple configuration.

When the second optometry unit 4b is stacked on or above the first optometry unit 4a and the face photographing unit 190 is placed at the height between the first optometry unit 4a and the second optometry unit 4b as shown in the foregoing example, the height of the face photographing unit 190 with respect to the examinee's eye is different between the measurement modes. In the first mode, for example, when the optical axis La of the first optometry unit 4a is adjusted to the height of the examinee's eye, the face photographing unit 190 is placed above the first optometry unit 4a and thus the optical axis L5 is positioned above the examinee's eye E. In this case, the direction V1 of the examinee's eye as seen from the face photographing unit 190 is an obliquely downward direction as shown in FIG. 7A. In the second mode, furthermore, when the optical axis Lb of the second optometry unit 4b is adjusted to the height of the examinee's eye, the face photographing unit 190 is placed below the second optometry unit 4b and thus the optical axis L5 is positioned above below the examinee's eye E. In this case, the direction V2 of the examinee's eye as as seen from the face photographing unit 190 is an obliquely upward direction as shown in FIG. 7B. Accordingly, the controller 20 can switch the movement direction of the optometry unit 4 according to the measurement mode to appropriately move the first optometry unit 4a or the second optometry unit 4b with respect to the examinee's eye.

The controller 20 may also be configured to make a measurement of both eyes in such a manner that, upon completion of measurement of one eye, alignment with the other eye is automatically performed. In the first mode or the second mode, for instance, the refractive power measurement or the intraocular pressure measurement of a right eye is performed first and, after the termination of the right eye measurement, the refractive power measurement or the intraocular pressure measurement of a left eye may be started. In the third mode, the measurement may be proceeded by measuring the refractive power and the intraocular pressure of a right eye and then those of a left eye or by measuring the refractive power of right and left eyes and then the intraocular pressure of the right and left eyes. Of course, the measurement may also begin with either a right eye or a left eye.

<Calculation of Examinee's Eye Direction as Seen from Face Photographing Unit>

A method of calculating the examinee's eye direction as seen from the face photographing unit 190 will be described below. The controller 20 obtains the direction of the examinee's eye E as seen from the face photographing unit 190 based on the face image P2 photographed by the face photographing unit 190. The examinee's eye direction is for example a three-dimensional direction (e.g. a space vector).

The controller 20 calculates the coordinate $(x_e, y_e)$ of the examinee's eye (e.g. a pupil) on the face image P2. For instance, this coordinate of the examinee's eye may be obtained by analysis of the luminance and the edge of the face image P2, and others.

Herein, assuming that the three-dimensional coordinate of the examinee's eye E is $(X_e, Y_e, Z_e)$, the relationship between the coordinate $(x_e, y_e)$ thereof on the face image P2 and an actual coordinate $(X_e, Y_e, Z_e)$ of the eye E is expressed by Equation 1:

$$h \begin{pmatrix} x_e \\ y_e \\ 1 \end{pmatrix} = \begin{pmatrix} f_x & s & c_x \\ 0 & f_y & c_y \\ 0 & 0 & 1 \end{pmatrix} \begin{pmatrix} r_{11} & r_{12} & r_{13} & t_X \\ r_{21} & r_{22} & r_{23} & t_Y \\ r_{31} & r_{32} & r_{33} & t_Z \end{pmatrix} \begin{pmatrix} X_e \\ Y_e \\ Z_e \\ 1 \end{pmatrix} \quad \text{(Eq. 1)}$$

In Equation 1, Equation 2 is a camera internal parameter:

$$\begin{pmatrix} f_x & s & c_x \\ 0 & f_y & c_y \\ 0 & 0 & 1 \end{pmatrix} \quad \text{(Eq. 2)}$$

where $f_x$ and $f_y$ denote a focal point distance, s denotes skew distortion, and $(c_x, c_y)$ denotes an optical center on the image. These values are obtained by performing calibration of the face photographing unit 190 in advance. Further, Equation 3 is a camera external parameter:

$$\begin{pmatrix} r_{11} & r_{12} & r_{13} & t_X \\ r_{21} & r_{22} & r_{23} & t_Y \\ r_{31} & r_{32} & r_{33} & t_Z \end{pmatrix} \quad \text{(Eq. 3)}$$

and Equation 4 is a rotational component of the face photographing unit 190:

$$\begin{pmatrix} r_{11} & r_{12} & r_{13} \\ r_{21} & r_{22} & r_{23} \\ r_{31} & r_{32} & r_{33} \end{pmatrix} \quad \text{(Eq. 4)}$$

where $(t_X, t_Y, t_Z)$ denotes a parallel displacement component of the face photographing unit 190 (the position of the face photographing unit 190). Further, h denotes an arbitrary scale.

Herein, the position of the examinee's eye E as seen from the face photographing unit 190 is assumed as $E'=(X_e', Y_e', Z_e')=(X_e-t_X, Y_e-t_Y, Z_e-t_Z)$. From this, the direction of the examinee's eye as seen from the face photographing unit 190 is the direction vector V of E'. Herein, from Equation 1, Equation 5 is established:

$$h' \begin{pmatrix} x_e \\ y_e \\ 1 \end{pmatrix} = \begin{pmatrix} f_x & s & c_x \\ 0 & f_y & c_y \\ 0 & 0 & 1 \end{pmatrix} \begin{pmatrix} r_{11} & r_{12} & r_{13} \\ r_{21} & r_{22} & r_{23} \\ r_{31} & r_{32} & r_{33} \end{pmatrix} \begin{pmatrix} X_e' \\ Y_e' \\ Z_e' \end{pmatrix} \quad \text{(Eq. 5)}$$

Herein, the ratio of $X_e':Y_e':Z_e'$ has only to be obtained in order to calculate the direction vector V of E' and thus substitution of $X_e'=mZ_e$ and $Y_e'=nZ_e$ into Equation 5 results in Equation 6:

$$h'\begin{pmatrix} x_e \\ y_e \\ 1 \end{pmatrix} = \begin{pmatrix} f_x & s & c_x \\ 0 & f_y & c_y \\ 0 & 0 & 1 \end{pmatrix} \begin{pmatrix} r_{11} & r_{12} & r_{13} \\ r_{21} & r_{22} & r_{23} \\ r_{31} & r_{32} & r_{33} \end{pmatrix} \begin{pmatrix} m \\ n \\ 1 \end{pmatrix} \quad \text{(Eq. 6)}$$

where $h'=h/Z_e$. This equation includes three unknown letters; h', m, and n. The values m and n are designated by solving simultaneous equations developed from Equation 6. Accordingly, the ratio of $X_e':Y_e':Z_e'$ is obtained and thus the direction vector V of E' is obtained. As above, the controller 20 determines the direction of the examinee's eye as seen from the face photographing unit 190. For the alignment method using the face photographing unit 190, Japanese unexamined patent application publication No. 2017-64058 may also be referred to.

REFERENCE SIGNS LIST

1 Ophthalmic apparatus
2 Drive unit
4 Optometry unit
4a First optometry unit
4b Second optometry unit
5 Base table
6 Housing
9 Face support unit
13 Z-drive unit
20 Controller
21 CPU
22 ROM
23 RAM
24 Storage unit
190 Face photographing unit
La Measurement optical axis of first optometry unit
Lb Measurement optical axis of second optometry unit

What is claimed is:

1. An ophthalmic apparatus configured to examine an eye of an examinee, the apparatus comprising:
   a first optometry unit configured to perform a first examination of the examinee's eye;
   a second optometry unit configured to perform a second examination of the examinee's eye;
   a drive unit configured to move the first optometry unit and the second optometry unit in three-dimensions relative to a position of the examinee's eye;
   a selection receiving unit configured to receive a selection signal representing at least one of the first examination and the second examination;
   a face photographing unit configured to photograph a face image including at least one of right and left eyes of the examinee; and
   a controller configured to:
      control the drive unit to move the first optometry unit and the second optometry unit, and
      switch, according to the selection signal, between a first path for alignment of the first optometry unit with the examinee's eye detected from the face image and a second path for alignment of the second optometry unit with the examinee's eye detected from the face image, wherein
   a height of an optical axis of the face photographing unit is at a height between (a) a first optical axis corresponding to an examination optical axis of the first optometry unit and (b) a second optical axis corresponding to an examination optical axis of the second optometry unit, and
   the optical axis of the face photographing unit is not coaxial with either of the first optical axis and the second optical axis.

2. The ophthalmic apparatus according to claim 1, wherein
   the controller is configured to:
      determine the first path based on a relative position between the first optometry unit and the face photographing unit, and
      determine the second path based on a relative position between the second optometry unit and the face photographing unit.

3. The ophthalmic apparatus according to claim 1, wherein the controller is configured to move the first optometry unit and the second optometry unit to an initial position different between when the first examination is performed and when the second examination is performed.

4. The ophthalmic apparatus according to claim 1, wherein the controller is configured to set a moving speed to move the first optometry unit and the second optometry unit such that the moving speed is different between the first path and the second path.

5. The ophthalmic apparatus according to claim 4, wherein
   the first optometry unit is an eye refractive power measuring unit configured to measure eye refractive power of the examinee's eye,
   the second optometry unit is an intraocular pressure measuring unit configured to measure intraocular pressure of the examinee's eye, and
   the controller is configured to set the moving speed in the second path slower than the moving speed in the first path.

6. The ophthalmic apparatus according to claim 1, wherein the second optical axis is located at a higher position than the first optical axis.

7. The ophthalmic apparatus according to claim 1, wherein an entirety of the optical axis of the face photographing unit is spaced from the first optical axis and from the second optical axis.

* * * * *